US006968729B1

(12) United States Patent
Karlsson et al.

(10) Patent No.: US 6,968,729 B1
(45) Date of Patent: Nov. 29, 2005

(54) METHOD AND APPARATUS FOR EXPEDITING ANALYSIS OF SAMPLES

(75) Inventors: Arne Karlsson, Oslo (NO); Duncan E. Akporiaye, Arlington Heights, IL (US); Svend A. Taftø, Sandvika (NO); Ivar M. Dahl, Oslo (NO); Elisabeth M. Myhrvold, Jar (NO); Arne L. Kvernheim, Nesoddtangen (NO)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 10/789,663

(22) Filed: Feb. 27, 2004

(51) Int. Cl.⁷ .......................................... G01N 30/04
(52) U.S. Cl. .................. 73/23.41; 73/23.42; 73/23.22; 73/23.35
(58) Field of Search ............................ 73/23.41, 23.42, 73/23.22, 23.35

(56) References Cited

U.S. PATENT DOCUMENTS

| 3,220,164 | A | * | 11/1965 | Golay ............................ 95/84 |
| 3,236,603 | A | * | 2/1966 | Durrett et. al. ................ 422/89 |
| 3,394,582 | A | * | 7/1968 | Munro et al. .............. 73/23.41 |
| 3,431,077 | A | | 3/1969 | Danforth |
| 3,518,059 | A | * | 6/1970 | Levy ........................... 436/158 |
| 3,753,656 | A | * | 8/1973 | Matson et al. ................. 436/39 |
| 4,007,626 | A | | 2/1977 | Roof et al. |
| 4,099,923 | A | | 7/1978 | Milberger |
| 5,034,193 | A | * | 7/1991 | Maroulis et al. ............... 422/89 |
| 5,057,126 | A | | 10/1991 | Lubkowitz et al. |
| 5,281,256 | A | * | 1/1994 | Sacks et al. .................... 95/86 |
| 5,652,398 | A | * | 7/1997 | Johnson ................... 73/863.71 |
| 5,933,357 | A | | 8/1999 | Tipler |
| 6,491,816 | B2 | | 12/2002 | Petro |
| 2002/0014106 | A1 | | 2/2002 | Srinivasan et al. ......... 73/23.42 |

FOREIGN PATENT DOCUMENTS

WO  WO 01/44801 A2  12/2000

OTHER PUBLICATIONS

Journal of Chromatography A, 654 (1993), 287-298.

* cited by examiner

*Primary Examiner*—Michael Cygan
(74) *Attorney, Agent, or Firm*—John G. Tolomei; Maryann Maas (57) ABSTRACT

The present invention comprises a method for expediting the analysis of a plurality of samples, preferably using gas chromatography. A specific embodiment comprises a dual isothermal heated zone configuration for use in combinatorial chemistry. This involves partitioning the samples into two isothermal zones, allowing detailed analysis of light components in a lower-temperature zone while heavy components are handled in a higher-temperature zone.

29 Claims, 5 Drawing Sheets

METHOD AND APPARATUS FOR EXPEDITING ANALYSIS OF SAMPLES

FIELD OF THE INVENTION

The present invention relates to the use of high-speed analytical techniques to analyze the composition of samples. More specifically, the invention relates to a method of obtaining high-speed analyses of samples containing low-boiling and high-boiling components using gas chromatography.

BACKGROUND OF THE INVENTION

The development of highly optimized chemical processes requires sophisticated analytical techniques to distinguish between optimum reactants, conditions and catalysts. These analytical techniques must be fast as well as accurate to deal with an increasing amount of data associated with the optimization. Gas chromatography in particular is widely used to assess the composition of products from chemical processes, but generally is slower than the tests used to effect chemical reactions. Combinatorial chemistry, in particular, provides a large number of samples to be analyzed in order to draw conclusions.

Combinatorial chemistry enables the formation of a large number of products from a relatively smaller number of precursors, thus facilitating the rapid comparison of a variety of methods, materials and products. This technique has become essential in the field of drug discovery, enabling the synthesis of large libraries of organic molecules for evaluation. More recently, combinatorial methods have been applied to the synthesis of chemical compounds and evaluation of libraries of catalytic materials and conditions for such syntheses. Developments in combinatorial chemistry thus have effected a need for high-speed analytical methods to carry out such evaluations.

An early illustration of the principle of combinatorial chemistry and associated analyses in chemical syntheses is U.S. Pat. No. 3,431,077, which discloses an analytical apparatus comprising a plurality of chambers containing test materials and connected by a relatively short passage to a chromatographic column. U.S. Pat. No. 4,099,923 teaches an automatic catalyst screening unit comprising a plurality of reaction chambers communicating via a common manifold with an analyzing means which sequentially analyzes product from each of the plurality of reactors; analysis of the reaction product may be effected by a gas chromatograph. WO 01/44801 A2 discloses testing of a plurality of catalysts using combinatorial chemistry wherein each of the catalyst beds is fluidized, and each of the effluents is analyzed to determine its chemical composition with chromatography being a preferred method of analysis.

The problem of rapidly screening large numbers of samples by liquid chromatographic techniques requiring up to an hour for each sample is recognized in U.S. Pat. No. 6,491,816 B2, which teaches parallel chromatographic columns with staggered parallel separation. U.S. Pat. No. 4,007,626 teaches chromatographic analysis of the volatile components in a sample having both volatile and nonvolatile components by vaporizing the sample, passing the vapor through a first chromatographic column to separate the constituents to be determined, and analyzing such constituents in a second chromatographic column while backflushing the first chromatographic column. High-throughput screening of catalysts using gas chromatography is addressed in U.S. Publication 2002/0014106 A1, through the use of highly parallel gas chromatographs (four or more columns) and microdetector arrays integrated with parallel reactors. In a situation wherein only the more volatile components of a sample are of interest, U.S. Pat. No. 5,057,126 discloses sequential injection of the sample into hot and lower-temperature vaporization chambers containing packing material, with the more volatile relevant components passing to a chromatographic column with the vaporization chambers being backflushed. U.S. Pat. No. 5,933,357 teaches a dual column gas chromatography system including a precolumn followed by a separating column and a method of establishing the retention times of components eluting from the partitioning in order to determine the optimum backflush point. The use of a backflushed precolumn to remove non-volatile material from samples prior to gas chromatography is taught by Gunnar Hagman and Johan Roeraade in "Online liquid backflush of an uncoated precolumn for automated gas chromatographic analysis of complex mixtures," Journal of Chromatography A, 654 (1993), 287–298.

The art does not suggest, however, a method for expediting the analysis of all relevant components in a sample containing both low-boiling and high-boiling components.

SUMMARY OF THE INVENTION

The present invention provides a means for expediting the analysis of samples containing both relevant low-boiling and relevant high-boiling components. More specifically, the invention provides expedited analysis of the samples by gas chromatography by fractionating the relevant components in the samples prior to chromatographic analysis in order to shorten the time for these components to traverse a chromatographic column. Through such expediting, the invention achieves one or more of:

reducing the amount of analytical equipment required to obtain the analysis, and shortening the waiting time for the analysis of a plurality of samples which are analyzed sequentially.

In a broad embodiment, a sample is fractionated to obtain a low-boiling fraction containing at least one relevant low-boiling component and a high-boiling fraction containing at least one relevant high-boiling component, each of which fractions are analyzed in one or more analysis zones which determine the at least one relevant component in each fraction.

In a more specific embodiment, a sample is fractionated to obtain a low-boiling fraction containing at least one relevant low-boiling component and a high-boiling fraction containing at least one relevant high-boiling component; the low-boiling fraction is analyzed using gas chromatography to determine the at least one relevant low-boiling component, while the high-boiling fraction is analyzed in a second analysis zone to determine the at least one relevant high-boiling component.

In another specific embodiment, a sample is fractionated to obtain a low-boiling fraction containing at least one relevant low-boiling component and a high-boiling fraction containing at least one relevant high-boiling component; the low-boiling fraction is analyzed by gas chromatography to determine the at least one relevant low-boiling component, while the high-boiling fraction is analyzed by gas chromatography to determine the at least one relevant high-boiling component.

In yet another specific embodiment, a sample is fractionated in a fractionation zone comprising gas chromatography at isothermal conditions to obtain a low-boiling fraction containing at least one relevant low-boiling component and a high-boiling fraction containing at least one relevant high-boiling component; the low-boiling fraction is analyzed by gas chromatography to determine the at least one relevant low-boiling component, while the high-boiling fraction is analyzed by gas chromatography to determine the at least one relevant high-boiling component.

In yet another specific embodiment, a sample is fractionated in a fractionation zone comprising gas chromatography at isothermal conditions to obtain a low-boiling fraction containing at least one relevant low-boiling component and a high-boiling fraction containing at least one relevant high-boiling component; the low-boiling fraction is analyzed by gas chromatography to determine the at least one relevant low-boiling component, while the high-boiling fraction is backflushed from the chromatographic prefractionator to a second analysis zone to determine the at least one relevant high-boiling component.

In an alternative embodiment, a plurality of samples obtained by combinatorial chemistry are sequenced through a sampling valve and fractionated using gas chromatography to obtain a plurality of low-boiling fractions containing at least one relevant low-boiling component and a plurality of high-boiling fractions containing at least one relevant high-boiling component; the plurality of low-boiling fractions are analyzed by gas chromatography to determine the at least one relevant low-boiling component, while the plurality of high-boiling fractions are analyzed in a second analysis device to determine the at least one relevant high-boiling component.

In yet another alternative embodiment, a plurality of samples obtained by combinatorial chemistry are fractionated in a chromatographic prefractionator at isothermal conditions to obtain a plurality of low-boiling fractions containing at least one relevant low-boiling component and a plurality of high-boiling fractions containing at least one relevant high-boiling component; the plurality of low-boiling fractions are analyzed by gas chromatography to determine the at least one relevant low-boiling component, while the plurality of high-boiling fractions are backflushed from the fractionation zone and analyzed in a second analysis device to determine the at least one relevant high-boiling component.

In a specific embodiment involving combinatorial chemistry, a feed fluid is contacted simultaneously with a plurality of solids, each solid being housed in an individual vessel to generate a plurality of vessel effluents which are sampled simultaneously to provide a plurality of samples. The plurality of samples are fractionated by gas chromatography at isothermal conditions to obtain a plurality of low-boiling fractions containing at least one relevant low-boiling component and a plurality of high-boiling fractions containing at least one relevant high-boiling component; the plurality of low-boiling fractions are analyzed by gas chromatography to determine the at least one relevant low-boiling component, while the plurality of high-boiling fractions are backflushed from the fractionation zone and analyzed by gas chromatography to determine the at least one relevant high-boiling component.

In one more alternative embodiment, an apparatus comprises a fractionation zone comprising a chromatographic fractionator having an inlet and an outlet, a first analysis zone comprising a gas chromatograph having an inlet in communication with the outlet of the fractionation zone and an outlet in communication with a detector, a backflushing valve in communication with the fractionation zone, and a second analysis zone comprising an analysis device in communication with the outlet of the fractionation zone.

DETAILED DESCRIPTION OF THE INVENTION

In summary, the present invention provides a method for expedited analysis of samples by isolating the relevant low-boiling and high-boiling components in the samples prior to analysis in order to shorten the time for analysis of each of the relevant components. Although elements of the method and associated apparatus are described in the singular, it is to be understood that two or more parallel or series sets of each element or of the entire apparatus are within the scope of the invention.

By "sample" is meant a mixture of organic compounds whose analysis is desired for evaluation of a chemical or biological process to determine one or more of optimum reactants, conditions and catalysts. A sample may contain one or more of a variety of moieties, including but not limited to hydrocarbons, oxides, alcohols, ketones, esters, acids, bases, sulfides, sulfates, halides, metal-organic compounds and the like. Hydrocarbons are preferred components of samples.

A "relevant" component is a compound whose presence, and especially concentration, in the sample is important to the analysis. Each sample of the invention contains at least one relevant low-boiling component and at least one relevant high-boiling component, e.g., whose respective distillation temperatures are low and high relative to each other. "Last relevant low-boiling component" refers to the highest-boiling relevant component in the low-boiling fraction, whose separation into the low-boiling fraction indicates that the fractionation has been completed.

"Fractionation" of the sample refers to any means effective to separate a low-boiling fraction from a high-boiling fraction of the sample, including but not limited to distillation, vapor-liquid separation, and chromatographic separation. Chromatographic separation is a preferred method of the invention, and the following description of the invention is based on the use of gas chromatography in fractionation. The low-boiling fraction from fractionation contains at least one relevant low-boiling component, and the high-boiling fraction contains at least one relevant high-boiling component.

"Analysis" of the sample in an analysis zone is effected to provide the pertinent data relating to the presence and concentration of relevant components. "Analysis" of a fraction of the sample may comprise one or both of separation and of characterization of the fraction using chromatography and other techniques described herein.

The present invention is particularly useful in combinatorial chemistry, wherein a plurality of samples are generated for which analysis is required to evaluate the process, conditions and feedstocks being tested. Combinatorial chemistry is described inter alia in International Publication WO 01/44801 A2 and U.S. Pat. No. 6,368,865 B1, both incorporated herein by reference thereto. Preferably the present invention is used to assess the performance and optimum conditions of use of a multiplicity of solids. The plurality of samples of the present invention in this case are selected from effluents from the processing of one or more feeds to the multiplicity of solids. Catalytic activity and selectivity of a solid may be evaluated by analyzing the concentration of components in each sample of reactor effluent compared to concentrations in the feed. Similarly, adsorptivity of solids may be evaluated by comparing the concentration of an adsorbate in effluent samples relative to concentrations in the feed. The effluents from the processing of one or more feeds over a multiplicity of solids then become the source of the plurality of samples analyzed through the present invention.

In a preferred embodiment, a multiplicity of catalysts are tested in an array of reactors to generate a plurality of effluents from which a plurality of samples are selected for analysis. The array of reactors comprises two (2) or more reactors, generally four (4) or more, usually six (6) or more, and more often at least eight (8) reactors. Typically, but without limitation, some multiple of these numbers of reactors is contained in the array such as 12, 24, 48, 96, 392, or 1264 arranged in a row-and-column formation similar to that of a microtiter tray.

This combinatorial chemistry approach thus generates a plurality of samples to be analyzed according to the present invention. A "plurality" encompasses at least four (4), more usually six (6) or more, generally at least eight (8), and optionally forty-eight (48) or more samples. If such samples are selected and analyzed as generated using parallel analysis equipment (e.g., gas chromatographs), the corresponding plurality of analytical instruments required would be very costly.

More usually, the samples are generated simultaneously and analyzed sequentially in a smaller number of analytical instruments, i.e., one sample is selected for analysis while other of a plurality of samples are held for subsequent analysis. In this case, either the plurality of effluents must be stored for sequential sampling or the effluents must be sampled with the samples being stored for later analysis. In this case, it further is desirable to minimize the time that effluents or samples are held for analysis in order to use the combinatorial array effectively and avoid affecting analytical results through any side reactions that may occur during the holding time. The present invention mitigates concerns about holding time and/or the cost of analytical equipment by optimizing the respective analyses of low-boiling and high-boiling fractions.

The plurality of samples preferably are provided in gaseous form, but it is within the scope of the invention that liquid samples may be analyzed. Selection of one sample from a plurality of samples to the process of the invention may be effected using any type of device that enables the selected sample to be directed to analysis and the remainder of the samples isolated for later analysis. An effective sampling system of sampling valves is shown in copending application U.S. Publication 2003/0053937 A1, incorporated herein in its entirety by reference thereto, with particular attention to FIGS. 2 and 3 and related text. It is within the scope of the present invention to utilize sampling valves that simultaneously select two or more samples for parallel analysis when multiple process trains are provided.

Figure 1A:
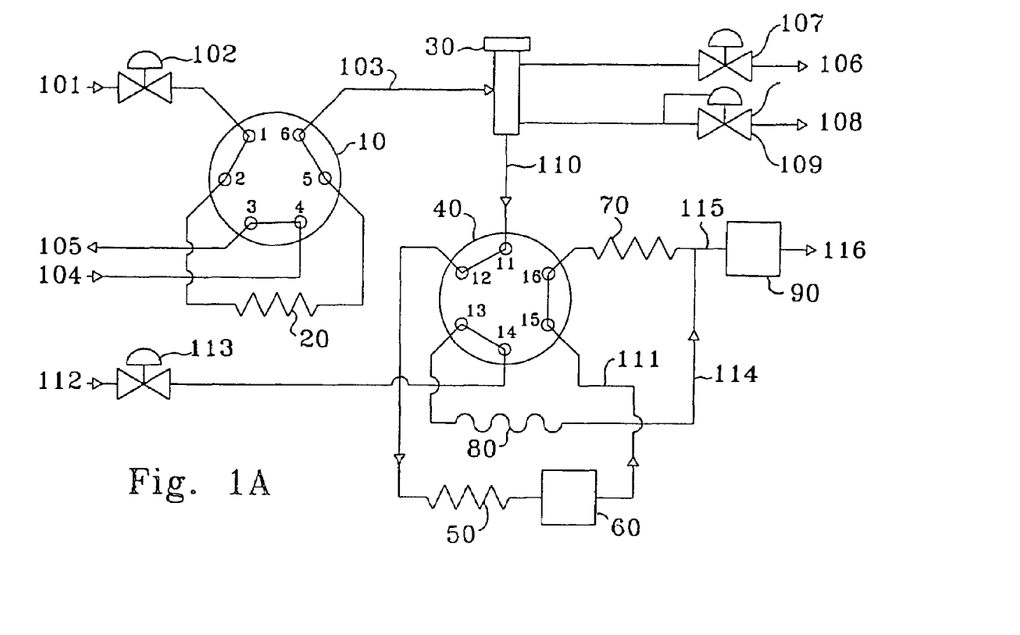
FIG. 1A illustrates the principles of the process of the invention in sample-transfer mode
Figure 1B:
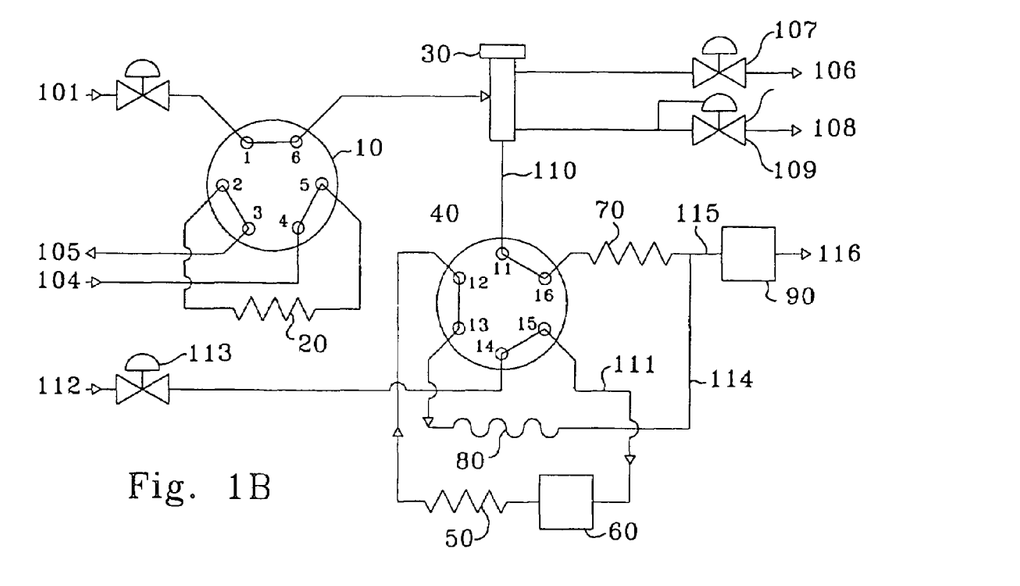
FIG. 1B is a backflush-mode illustration corresponding to FIG. 1A.

An embodiment of the present invention is illustrated in FIGS. 1A and 1B which respectively show different modes of the method of the invention. FIG. 1A shows principal valves in sample-transfer mode, conducting a sample through a fractionation zone and an analysis zone of the invention comprising a detector. FIG. 1B shows principal valves in backflush mode, backflushing a high-boiling component to the detector.

In FIG. 1A, a carrier gas in stream 101 controlled by valve 102 flows through ports 1 and 2 of sample-injection valve 10, conducting a sample contained in sample loop 20 through ports 5 and 6 of valve 10 into line 103. Additional sample contained in line 104 flows through ports 3 and 4 of valve 10 and is vented via line 105. The combined gas stream and sample flow through line 103 to injector port 30. The septum of the injector port is purged via line 106 and valve 107, and vent 108 controls the flow via valve 109 of combined stream 110 from the injector port. The combined gas stream and sample flow via line 110 through ports 11 and 12 of backflush valve 40 to fractionation zone 50. The fractionation zone separates the sample into a low-boiling fraction, which passes from the zone in line 111, and a high-boiling fraction. Preferably fractionation zone 50 employs gas chromatography as a chromatographic fractionator to separate the low-boiling fraction from the high-boiling fraction, and the high-boiling fraction remains in the fractionation zone during the present sample-transfer mode. Optional detector 60 is used to determine when the last relevant low-boiling component has passed from the fractionation zone; the detector may be eliminated or bypassed in the event that fractionation zone conditions such as temperature and pressure have been standardized such that the time of passage, preferably elution, of the last relevant component is known without a detector.

Continuing in FIG. 1A, the low-boiling fraction passes via line 111 through ports 15 and 16 of valve 40 to first analysis zone 70 in which the low-boiling fraction is analyzed to determine one or both of the presence and concentration of at least one relevant low-boiling component. Optionally, carrier gas flows via line 112 and valve 113 through ports 13 and 14 of valve 40, controlled by restrictor 80, through line 114 the exit of analysis zone 70. Preferably analysis zone 70 employs gas chromatography to separate relevant low-boiling components contained in the low-boiling fraction. In this preferred embodiment, the analyzed fraction and carrier gas pass via line 115 to detector 90 to detect one or both of the presence and concentration of at least one relevant low-boiling component, exiting to vent via line 116.

FIG. 1B displays the backflush mode of the elements of FIG. 1A. Thus equipment items and lines retain the same numerical designation as in FIG. 1A, even though their operating mode is changed as becomes clear from the description.

A new sample passes into sample loop 20 via line 104 and ports 2 and 3 of sample-injection valve 10, and is retained in the loop until the valve is returned to the sample-transfer mode as in FIG. 1A. The carrier gas in line 101 flows through ports 1 and 6 of sample-injection valve 10, line 103, injector port 30, and ports 11 and 16 of backflush port 40 to maintain the flow of the low-boiling fraction through analysis zone 70 until this is purged of the low-boiling fraction.

Continuing in FIG. 1B, carrier gas flows via line 112 and valve 113, through ports 14 and 15 of valve 40, in reverse direction from the FIG. 1A mode, through fractionation zone 50 to remove the high-boiling fraction which remained in the zone from mode 1A. Effluent from the fractionation zone is controlled by restrictor 80 to detector 90 for determination of one or both of the presence and concentration of at least one relevant high-boiling component, exiting to vent via line 116. This determination is effected after the carrier gas in line 110 has removed substantially all of the low-boiling fraction from analysis zone 70 via line 115.

Detector 90, as well as optional detector 60, may comprise one or more of flame ionization detection, flame emission detection, thermal conductivity detection, pulse discharge detection, election capture detection, and other suitable detectors known in the art to determine one or both of the quantity and composition of this fraction being analyzed. Flame ionization detection (FID) is particularly preferred. In the FIG. 1B backflush mode, detector 90 may comprise parallel detectors respectively for the low-boiling fraction from analysis zone 70 and the high-boiling fraction from line 114. These parallel detectors may be of the same type or of different types selected from the above list. Analysis of the high-boiling fraction may comprise gas chromatography and is considered a second analysis zone whether applied sequentially or in parallel. Each detector optionally is controlled by a microprocessor, which further may store any data generated by the detector.

As an alternative to analysis of the low-boiling and high-boiling fractions by gas chromatography as described above, other methods may be applied in characterizing these fractions. These include, without limitation, separation methods such as liquid chromatography and distillation; detection methods such as flame ionization detection, flame emission detection, thermal conductivity detection, pulse discharge detection, and election capture detection; and analysis methods such as infrared absorption spectroscopy, Raman spectroscopy, ultraviolet absorption spectroscopy, visible absorption spectroscopy, fluorescence spectroscopy, mass spectrometry, infrared thermography, nuclear magnetic resonance, emission spectroscopy, radiochemical methods, conductometric methods, electrogravimetric methods, coulometric methods, voltammetry, and combinations thereof. Generally it is preferred to have both activity and selectivity information and, in that case, the analytical technique would be selected to measure the quantity of the different components present in each effluent from the chromatographic column.

Each of the FIG. 1A/1B streams sample 105/105', septum purge 106/106", vent 108/108' and detector effluent 116/116' preferably is conducted to a proper vent system. The system may include a knock-out pot to remove liquid. Depending upon the compounds in these streams, waste effluent optionally is treated to remove, convert, or neutralize specific contaminants.

The carrier gas may be any gas which does not react with the sample and can be distinguished from sample components in the detector, such as hydrogen, helium, nitrogen, carbon dioxide, and the like. A preferred carrier gas comprises one or both of hydrogen and helium. Alternatively, the invention as described may be applied in liquid chromatography; in this case, an inert liquid such as light paraffins or aromatic compounds may be substituted for or provided in addition to the carrier gas.

The exact type of valves 10 and 40 as described in FIGS. 1A/1B hereinabove will vary with the application. Suitable examples include Valco high-temperature and high-pressure valves.

Fractionation conditions and analysis conditions include temperatures, pressures, flow rates, carrier gas rates and the like suited to the particular process samples and objectives. Preferably one or both of the fractionation conditions and analysis conditions comprise isothermal conditions, i.e., one or both of the fractionation zone and analysis zone are maintained at a single temperature to effect the particular separation or analysis. Such temperatures generally are from about 25° to 350° C. and preferably between about 50° and 300° C. Isothermal fractionation-zone conditions preferably comprise a higher temperature than isothermal analysis-zone conditions, preferably at least about 25° C. higher. A heater or cooler, optionally utilizing a liquid bath, may be employed with a control device to maintain the fractionation and analysis zones, preferably comprising gas chromatography, at a desired temperature. Alternatively, the temperature of one or both of the fractionation zone and analysis zone may be ramped.

Preferably the selector and sampling valves, as well as the backflush valve, also are subjected to temperature control to maintain the isothermal conditions in the fractionation and analysis zones.

It is within the scope of the invention that a series of fractionation zones and analysis zones can be sequenced to expedite the analysis of a sample. The low-boiling fraction could be further fractionated in a sequential fractionation zone at sequential fractionation conditions to separate a lower-boiling fraction containing at least one relevant low-boiling component and an intermediate fraction containing at least one relevant intermediate component and analyzing the lower-boiling and intermediate fractions in sequential analysis zones to determine one or both of the presence and concentration of relevant low-boiling and intermediate components. The high-boiling fraction could be further fractionated in a sequential fractionation zone at sequential fractionation conditions to separate a higher-boiling fraction containing at least one relevant high-boiling component and an intermediate fraction containing at least one relevant intermediate component and analyzing the higher-boiling and intermediate fractions in sequential analysis zones to determine one or both of the presence and concentration of high-boiling and intermediate components. The intermediate fraction as well as the higher- and lower-boiling fractions could be further sequentially fractionated to separate additional fractions for analysis. The present invention is not limited to any number of sequential fractionation and analysis zones, although between two and 100 each of fractionation and analysis zones would cover the usual range of sequential zones.

Figure 2:
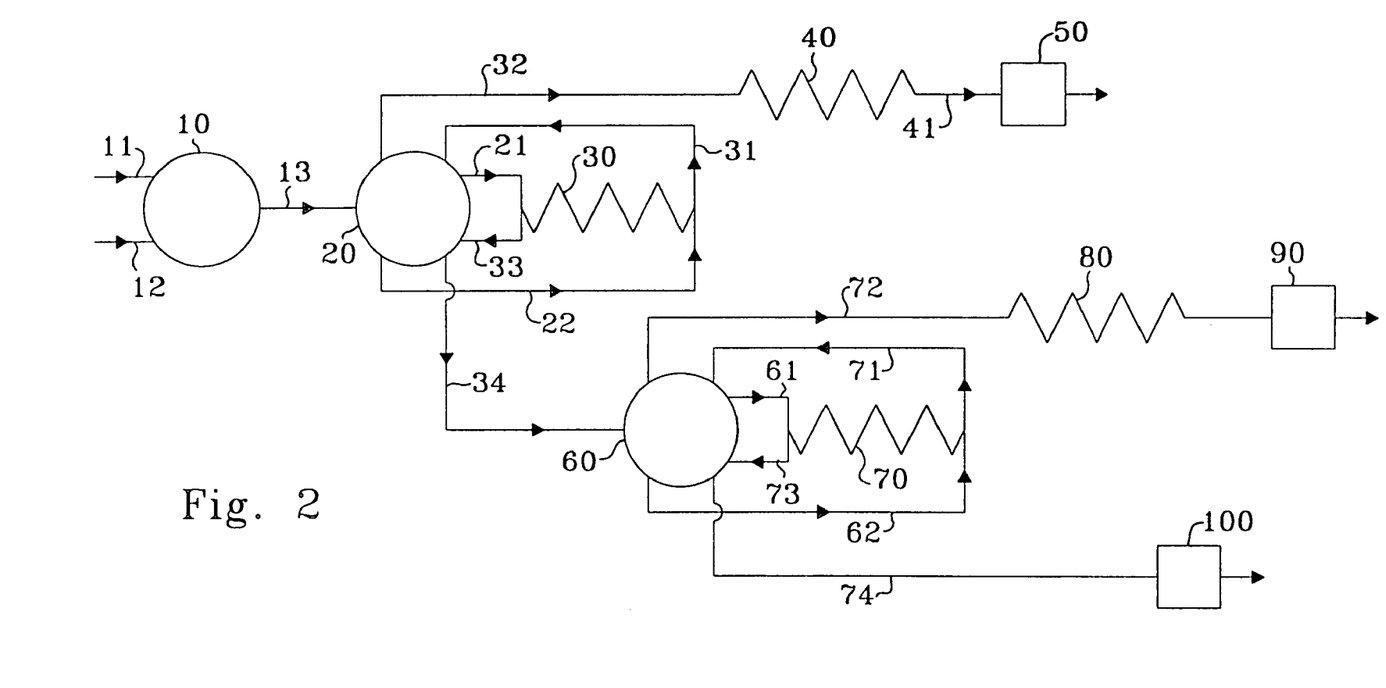
FIG. 2 illustrates the addition of fractionation and analysis of a high-boiling fraction to the basic invention.

For example, FIG. 2 is a simplified illustration of the sequential separation of a high-boiling fraction derived from the fractionation zone of FIGS. 1A/1B to provide an intermediate fraction to analysis. Selector/sampling valves represented by designation 10 process carrier gas 11 and sample 12, which are sent via 13 to backflush valve 20. In the mode of FIG. 1A, the combined carrier gas and sample are sent via 21 to a fractionation zone 30 which separates a low-boiling fraction 31. The low-boiling fraction is transmitted via the backflush valve in 32 to analysis zone 40, preferably a gas chromatograph, which analyzes the low-boiling fraction via 41 to detector 50. In the backflush mode of FIG. 1B, carrier gas is sent via 22 to fractionation zone 30 from which a high-boiling fraction is recovered via 33 through the backflush valve. The high-boiling fraction is sent via 34 to backflush valve 60. The high-boiling fraction and carrier gas are sent via 61 to a second fractionation zone 60 which separates an intermediate fraction 71 which contains at least one relevant intermediate component. The intermediate fraction is transmitted via the backflush valve in 72 to sequential analysis zone 80, preferably a gas chromatograph, which analyzes the intermediate fraction via 81 to detector 90 to determine one or both of the presence and concentration of the at least one intermediate component. In the backflush mode, carrier gas is sent via 62 to fractionation zone 70 from which a higher-boiling fraction is recovered via 73 through the backflush valve and 74 to detector 100 to determine one or both of the presence and concentration of at least one high-boiling component. Preferably analysis zones 40 and 80 employ gas chromatography, and optimally fractionation zones 30 and 70 also employ gas chromatography.

Figure 3:
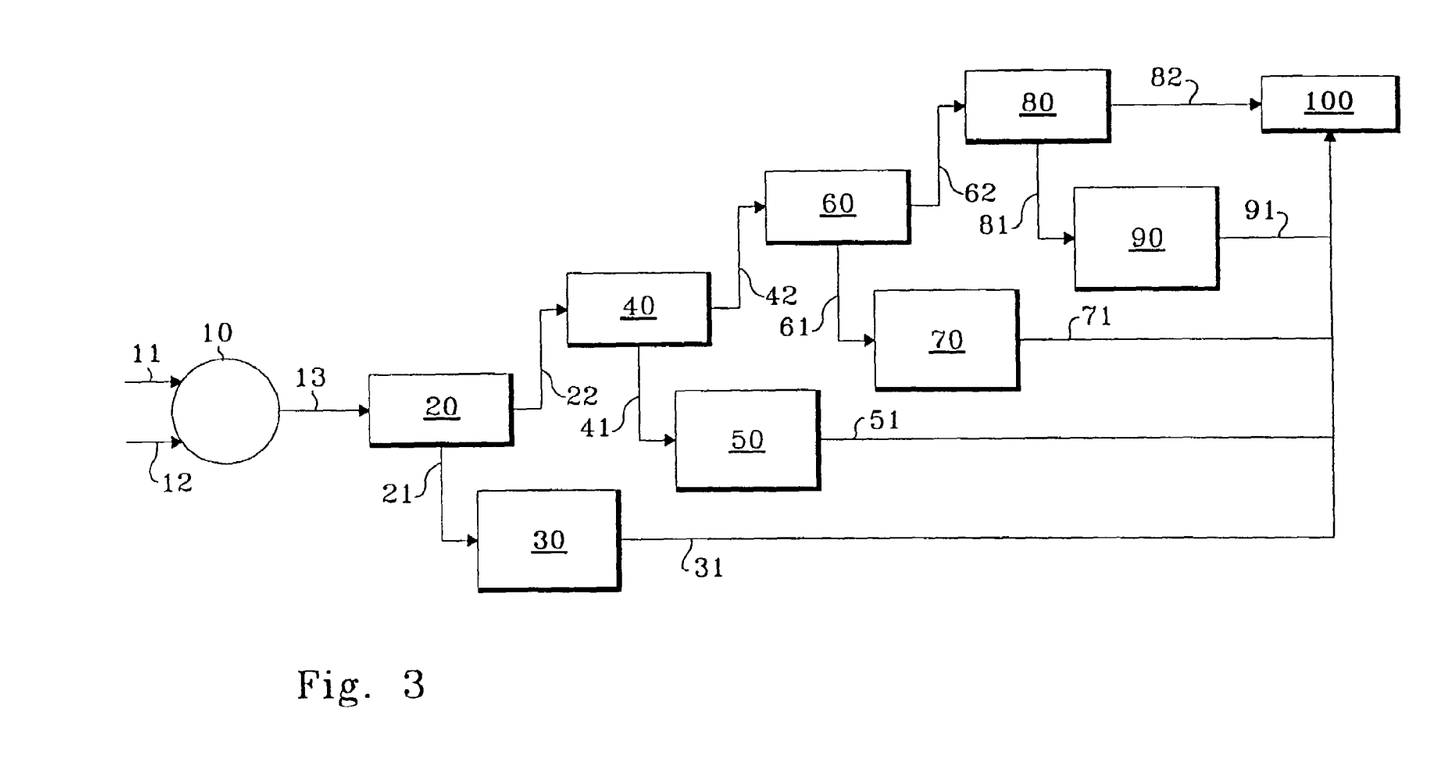
FIG. 3 shows sequential fractionation and analysis of a sample in several stages.

FIG. 3 is a further illustration of sequential fractionation and analysis zones. Backflush valves, understood from the prior text, are not shown in this illustration in order to feature the principles of this aspect of the invention. Selector/sampling valves 10 process carrier gas 11 and sample 12, which are sent via 13 to fractionation zone 20. The fractionation zone separates a high-boiling fraction 21 from a low-boiling fraction 22, and the high-boiling fraction is sent to analysis zone 30 yielding stream 31. The low-boiling fraction 22 is sent to a fractionation zone 40 which separates an intermediate fraction 41 containing at least one relevant intermediate component from a lower-boiling fraction 42 containing at least one relevant low-boiling component, and the high-boiling fraction is sent to analysis zone 50 yielding stream 51. The lower-boiling fraction 42 is sent to a fractionation zone 60 which separates an intermediate fraction 61 from a further lower-boiling fraction 62, and the high-boiling fraction is sent to analysis zone 70 yielding stream 71. The further lower-boiling fraction 62 is sent to a fractionation zone 80 which separates an intermediate fraction 81 from a further lower-boiling fraction 82, and the intermediate fraction is sent to analysis zone 90 yielding stream 91. Streams 31, 51, 71, 91 and 82 are sent to a detector, which may be multiple detectors or sequential processing in a single detector, to determine one or both of the presence and concentration of relevant low-boiling, intermediate and high-boiling components. Preferably analysis zones 30, 50, 70 and 90 employ gas chromatography, and optimally fractionation zones 20, 40, 60 and 80 also employ gas chromatography. The fractionation zones and analysis zones preferably employ isothermal conditions. It is especially preferred that fractionation zones 20, 40, 60 and 80 employ respectively lower temperatures in that sequence.

Examples were developed to show the advantage of the method of chromatographic analysis of the invention in comparison to the known art. The time required for an analysis of a hydrocarbon sample using gas chromatography was compared for the method of the invention relative and a conventional technique. The examples were developed using an aromatics mixture containing components, typically generated in a petrochemical process, as shown below in the following table:

| Component | Boiling Point, ° F. | Mol. Wt. |
|---|---|---|
| Nonaromatics + light ends | | |
| Benzene | 176.27 | 78.11 |
| Toluene | 231.13 | 92.13 |
| Ethylbenzene | 277.16 | 106.16 |
| p-Xylene | 281.05 | 106.16 |
| m-Xylene | 282.41 | 106.16 |
| Cumene | 306.34 | 120.20 |
| o-Xylene | 291.97 | 106.16 |
| n-propylbenzene | 318.63 | 120.20 |
| 1-methyl, 4-ethylbenzene | 323.62 | 120.20 |
| 1-lmethyl, 3-ethylbenzene | 322.39 | 120.20 |
| isobutylbenzene } peaks | 343.02 | 134.22 |

-continued

| Component | Boiling Point, ° F. | Mol. Wt. |
|---|---|---|
| tert-butylbenzene} co-elute | 336.47 | 134.22 |
| 1,3,5-trimethylbenzene | 328.54 | 120.20 |
| sec-butylbenzene | 344.00 | 134.22 |
| 1-methyl, 2-ethylbenzene | 329.32 | 120.20 |
| m-Cymene | 347.14 | 134.22 |
| p-Cymene | 350.83 | 134.22 |
| 1,2,4-trimethylbenzene | 336.88 | 120.20 |
| 1,2,3-trimethylbenzene | 349.01 | 120.20 |
| Other C4-benzenes | 352.7+ | 134.22 |
| Indane | 352.13 | 118.18 |
| C11 + Aromatics "green oils" | # | 148.25 |

Naphthalenes, anthracenes, coronenes, etc.

EXAMPLE 1

Figure 4:
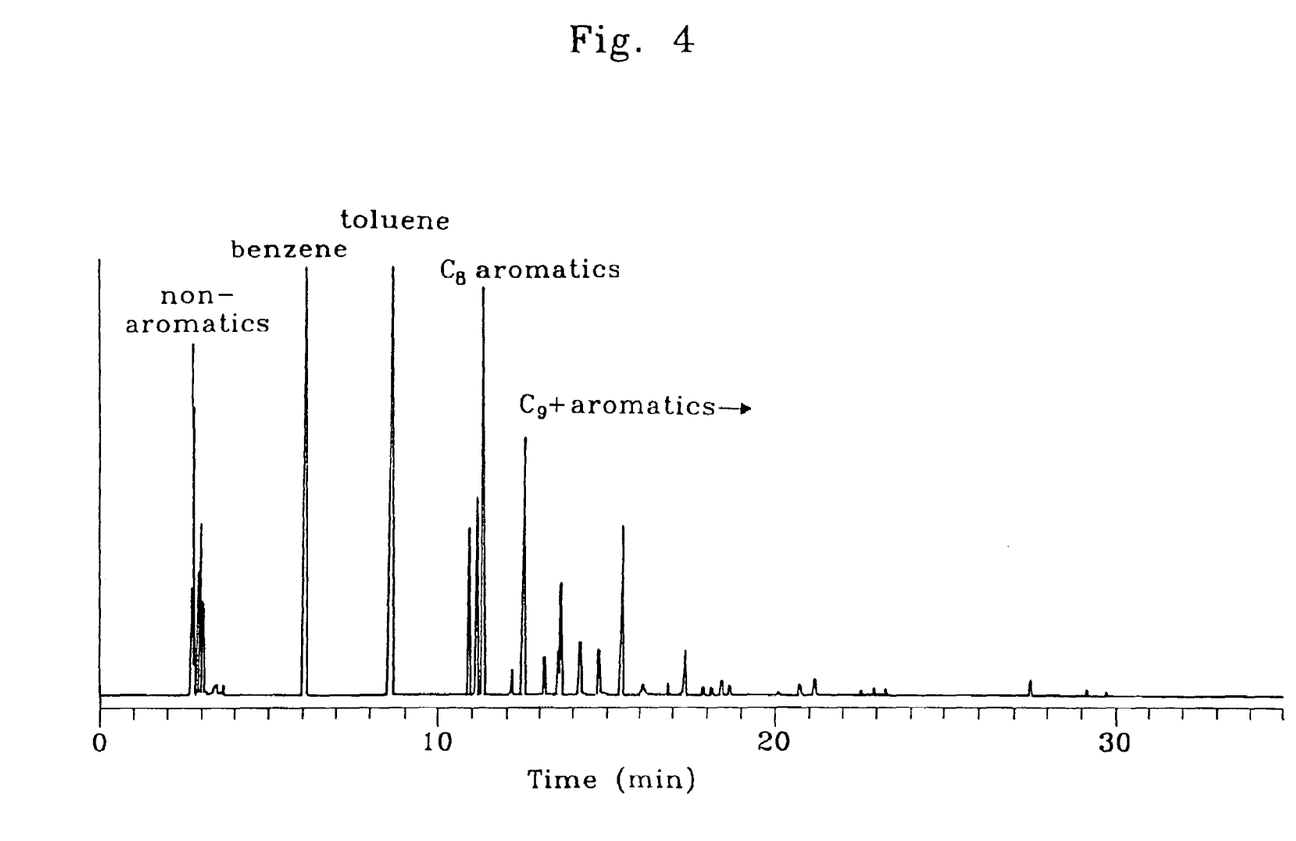
FIG. 4 is a chromatogram of a sample analyzed according to the known art.

In an embodiment of the known art, an aromatics mixture having components as identified in the previous table was subjected to gas chromatography to obtain the analysis illustrated in FIG. 4. The mixture was passed through a stainless steel tube having an internal diameter of 0.32 mm and a length of 60 meters which was coated with an 0.5 micron film of Supelcowax. The carrier gas was hydrogen at a pressure of 240 kPa, and the temperature was increased as follows:

5 minutes at 50° C.
8 minutes to 100° C.
2 minutes to 120° C.
20 minutes to 210° C.

Note that this chromatographic separation required about 35 minutes to complete, to which must be added at least 5 minutes for cooldown before a new analysis can be initiated. In the present case, as with many analyses of aromatic mixtures from petrochemical processes, detailed analyses are needed only for a limited range of components up through $C_6$, $C_7$, $C_8$ and $C_9$ aromatics; only the sum of the integrated areas of lighter and heavier components is of interest. Thus, considering aromatic components $C_6$ through $C_9$ in FIG. 4, the time required for the chromatographic analysis of Example I to quantify the components of interest is excessive for the data provided.

EXAMPLE 2

Figure 5:
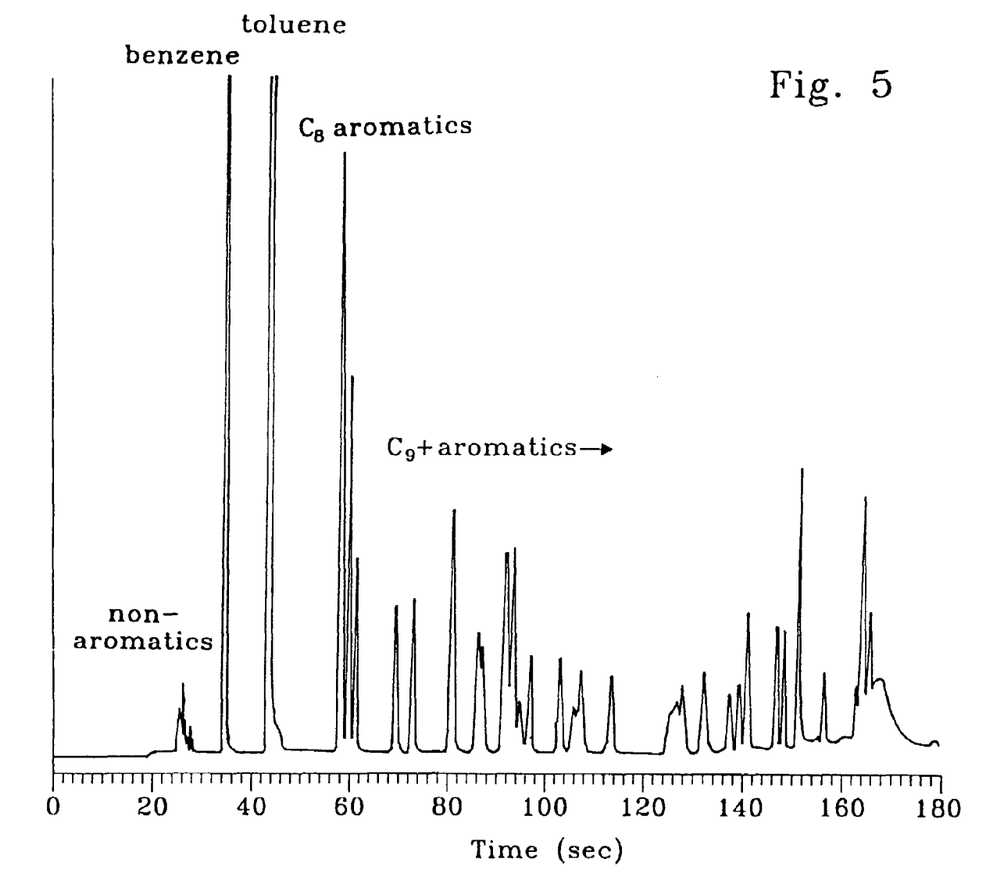
FIG. 5 is a chromatogram of a sample analyzed according to the present invention.

A contrasting chromatographic analysis of the present invention is shown in FIG. 5. An aromatic mixture containing components identified in the previous table was first subjected to fractionation at 200° C. in a precolumn (type CP-wax 52 CB, 5 meter, internal diameter 0.1 mm, coating: 0.2 mm layer) to separate the lighter components of interest from the heavier components in accordance with the method of the present invention described hereinabove without detailed analysis of the components. The heavier components then were backflushed for quantification as a group; alternatively, these backflushed heavy components could be separated in an additional high-temperature zone if detailed component analysis were to be desired.

The lighter components then were passed through a column of the type CP-wax 52 CB having an internal diameter of 0.10 mm and a length of 10 meters. The carrier gas was hydrogen and the column temperature was 70° C. The column pressure was 480 kPa for 2.13 minutes, then was ramped to 650 kPa at a ramp rate of 1030 kPa/minute where it remained for 0.87 minutes. The components of interest (benzene, toluene, $C_8$ and $C_9$ aromatics) were eluted over a time period of 150 seconds. In the present example (FIG. 5), the heavier components were backflushed for quantification as a group and revealed after 150 seconds in FIG. 5 as a broad peak in addition to less-well-defined peaks. In total, the analysis requires less than about 3 minutes as compared to the 35 minutes of FIG. 4. Further, since this analysis was carried out isothermally, the analytical instrument was ready for the next sample as soon as the analysis had been completed.

The savings in time through focusing the chromatographic analysis on components of interest and conducting the analysis isothermally as illustrated in FIG. 5 is particularly valuable in relation to combinatorial chemistry, where time is of the essence in obtaining results.

The above description and examples are intended to be illustrative of the invention without limiting its scope. The skilled routineer will readily understand how to extrapolate parameters of the disclosure to other embodiments of the invention. The invention is limited only by the claims set forth herein.

What is claimed is:

1. A method of expediting the analysis of a sample containing at least one relevant low-boiling component and at least one relevant high-boiling component comprising:
   a) fractionating the sample in a fractionation zone comprising gas chromatography at fractionation conditions to obtain a low-boiling fraction as elutrate containing the at least one relevant low-boiling component and a high-boiling fraction through backflushing containing the at least one relevant high-boiling component;
   b) fractionating the low-boiling component in a sequential fractionation zone which separates the low-boiling fraction at sequential fractionation conditions to obtain a lower-boiling fraction containing the at least one relevant low-boiling component and an intermediate fraction containing at least one relevant intermediate component;
   c) analyzing the lower-boiling fraction in a first analysis zone comprising gas chromatography at first analysis conditions to determine one or both of the presence and concentration of at least one relevant low-boiling component; and,
   d) analyzing the high-boiling fraction in a second analysis zone at second analysis conditions to determine one or both of the presence and concentration of at least one relevant high-boiling component.

2. The method of claim 1 wherein the second analysis zone comprises gas chromatography.

3. The method of claim 1 wherein at least one of the first analysis zone and second analysis zone comprise one or more of flame ionization detection, flame emission detection, thermal conductivity detection, pulse discharge detection, election capture detection, infrared absorption spectroscopy, Raman spectroscopy, distillation measurement, nuclear magnetic resonance, and mass spectrometry.

4. The method of claim 1 wherein the fractionation conditions, the sequential fractionation conditions and the first analysis conditions comprise isothermal conditions.

5. The method of claim 4 wherein the fractionation conditions comprise a higher temperature than that of the sequential fractionation conditions, and the sequential fractionation conditions comprise a higher temperature than that of the first analysis conditions.

6. A method of expediting the analysis of a sample containing at least one relevant low-boiling component and at least one relevant high-boiling component comprising:
   a) fractionating the sample in a fractionation zone comprising gas chromatography at fractionation conditions to obtain a low-boiling fraction as elutrate containing the at least one relevant low-boiling component and a high-boiling fraction through backflushing containing the at least one relevant high-boiling component;
   b) fractionating the low-boiling fraction in a sequential fractionation zone to separate the low-boiling fraction at sequential fractionation conditions to obtain a lower-boiling fraction containing the at least one relevant low-boiling component and an intermediate fraction containing at least one relevant intermediate component;
   c) analyzing the lower-boiling and intermediate fractions in sequential analysis zones wherein at least one analysis zone comprises gas chromatography to determine one or both of the presence and concentration of at least one relevant lower-boiling and intermediate components; and,
   d) analyzing the high-boiling fraction in a high-boiling fraction analysis zone at analysis conditions to determine one or both of the presence and concentration of at least one relevant high-boiling component.

7. The method of claim 6 wherein at least one of the analysis zones comprise one or more of gas chromatography, liquid chromatography, flame ionization detection, flame emission detection, thermal conductivity detection, election capture detection, infrared absorption spectroscopy, Raman spectroscopy, ultraviolet absorption spectroscopy, visible absorption spectroscopy, fluorescence spectroscopy, infrared thermography, nuclear magnetic resonance, emission spectroscopy, and mass spectrometry, as well as other radiochemical methods, electroanalytical methods, potentiometric methods, conductometric methods, electrogravimetric methods, coulometric methods, voltammetry and combinations thereof.

8. The method of claim 6 wherein at least one of the first analysis zones comprise gas chromatography plus one or more of flame ionization detection, flame emission detection, thermal conductivity detection, pulse discharge detection and election capture detection.

9. The method of claim 6 wherein at least one of the fractionation conditions comprise isothermal conditions.

10. The method of claim 9 wherein at least one analysis conditions comprise isothermal conditions.

11. The method of claim 6 further comprising between two and ten sequential fractionation and analysis zones.

12. A method of expediting the analysis of a sample containing at least one relevant low-boiling component and at least one relevant high-boiling component comprising:
   a) fractionating the sample in a fractionation zone comprising gas chromatography at fractionation conditions to obtain a low-boiling fraction as elutrate containing the at least one relevant low-boiling component and a high-boiling fraction through backflushing containing the at least one relevant high-boiling component;
   b) fractionating the high-boiling fraction in a sequential fractionation zone which separates the high-boiling fraction at sequential fractionation conditions to obtain a higher-boiling fraction containing at least one relevant high-boiling component and an intermediate fraction containing at least one relevant intermediate component;

c) analyzing the low-boiling fraction in a first analysis zone comprising gas chromatography at first analysis conditions to determine one or both of the presence and concentration of at least one relevant low-boiling component; and, d) analyzing the higher-boiling and intermediate fractions in a sequential analysis zone to determine one or both of the presence and concentration of at least one relevant higher-boiling and intermediate components.

13. The method of claim 12 wherein at least one of the analysis zones comprise one or more of gas chromatography, liquid chromatography, flame ionization detection, flame emission detection, thermal conductivity detection, election capture detection, infrared absorption spectroscopy, Raman spectroscopy, ultraviolet absorption spectroscopy, visible absorption spectroscopy, fluorescence spectroscopy, infrared thermography, nuclear magnetic resonance, emission spectroscopy, and mass spectrometry, as well as other radiochemical methods, electroanalytical methods, potentiometric methods, conductometric methods, electrogravimetric methods, coulometric methods, voltammetry and combinations thereof.

14. The method of claim 12 wherein at least one of the fractionation conditions comprise isothermal conditions and at least one of the analysis conditions comprise isothermal conditions.

15. The method of claim 12 further comprising between two and 100 sequential fractionation and analysis zones.

16. A method of expediting the analysis of a sample containing at least one relevant low-boiling component and at least one relevant high-boiling component comprising:

a) fractionating the sample in a fractionation zone comprising gas chromatography and fractionation conditions to obtain a low-boiling fraction as elutrate containing the at least one relevant low-boiling component and a high-boiling fraction through backflushing containing the at least one relevant high-boiling component;

b) fractionating the high-boiling fraction in a sequential fractionation zone to separate the high-boiling fraction at sequential fractionation conditions to obtain a higher-boiling fraction containing at least one relevant high-boiling component and an intermediate fraction containing at least one relevant intermediate component;

c) analyzing the low-boiling fraction in a first analysis zone at first analysis conditions to determine one or both of the presence and concentration of at least one relevant low-boiling component; and, d) analyzing the higher-boiling and intermediate fractions in sequential analysis zones wherein at least one analysis zone comprises gas chromatography to determine one or both of the presence and concentration of respective relevant high-boiling and intermediate components.

17. The method of claim 16 wherein at least one of the analysis zones comprise one or more of gas chromatography, flame ionization detection, flame emission detection, thermal conductivity detection, pulse discharge detection and election capture detection.

18. The method of claim 16 wherein the fractionation conditions comprise isothermal conditions.

19. The method of claim 18 wherein at least one of the analysis conditions comprise isothermal conditions.

20. The method of claim 16 further comprising between two and ten sequential fractionation and analysis zones.

21. A method of expediting the analysis of a plurality of samples containing at least one relevant low-boiling component and at least one relevant high-boiling component comprising:

a) fractionating the plurality of samples in a fractionation zone comprising gas chromatography at fractionation conditions to obtain a plurality of low-boiling fractions as elutrate containing the at least one relevant low-boiling component and a plurality of high-boiling fractions as backflush containing the at least one relevant high-boiling component;

b) fractionating the plurality of low-boiling fractions in a sequential fractionation zone to separate the low-boiling fractions at sequential fractionation conditions to obtain a plurality of lower-boiling fractions containing the at least one relevant low-boiling component and a plurality of intermediate fractions containing at least one relevant intermediate component;

c) analyzing the plurality of lower-boiling and intermediate fractions sequentially in sequential analysis zones to determine one or both of the presence and concentration of at least one relevant lower-boiling and intermediate components; and, d) analyzing the plurality of high-boiling fractions sequentially in a high-boiling fraction analysis zone at second analysis conditions to determine one or both of the presence and concentration of at least one relevant high-boiling component.

22. The method of claim 21 wherein at least one of the analysis zones comprise one or more of gas chromatography, flame ionization detection, flame emission detection, thermal conductivity detection, pulse discharge detection, election capture detection, infrared absorption spectroscopy, Raman spectroscopy, distillation measurement, nuclear magnetic resonance, and mass spectrometry.

23. The method of claim 21 wherein at least one of the fractionation conditions comprise isothermal conditions.

24. The method of claim 21 wherein at least one of the analysis conditions comprise isothermal conditions.

25. The method of claim 21 further comprising reacting a plurality of feedstocks at reaction conditions in a reaction zone comprising an array of reactors to obtain the plurality of samples, and directing the samples to a sampling valve to sequence the samples.

26. A method of expediting the analysis of a plurality of samples containing at least one relevant low-boiling component and at least one relevant high-boiling component comprising:

a) fractionating the plurality of samples in a fractionation zone comprising gas chromatography at fractionation conditions to obtain a plurality of low-boiling fractions as elutrate containing the at least one relevant low-boiling component and a plurality of high-boiling fractions as backflush containing the at least one relevant high-boiling component;

b) fractionating the plurality of high-boiling fractions in a sequential fractionation zone which separates the high-boiling fractions at sequential fractionation conditions to obtain a plurality of higher-boiling fractions containing at least one relevant high-boiling component and a plurality of intermediate fractions containing at least one relevant intermediate component;

c) analyzing the plurality of low-boiling fractions sequentially in a first analysis zone comprising gas chromatography at first analysis conditions to determine one or both of the presence and concentration of at least one relevant low-boiling component; and, d) analyzing the plurality of higher-boiling and intermediate fractions in a sequential analysis zone to determine one or both of the presence and concentration of at least one relevant higher-boiling and intermediate components.

27. The method of claim 26 wherein at least one of the analysis zones comprise one or more of gas chromatography, flame ionization detection, flame emission detection, thermal conductivity detection, pulse discharge detection, election capture detection, infrared absorption spectroscopy, Raman spectroscopy, distillation measurement, nuclear magnetic resonance, and mass spectrometry.

28. The method of claim 26 wherein at least one of the fractionation conditions comprise isothermal conditions and at least one of the analysis conditions comprise isothermal conditions.

29. The method of claim 26 further comprising reacting a plurality of feedstocks at reaction conditions in a reaction zone comprising an array of reactors to obtain the plurality of samples and directing the sample to a sampling valve to sequence the samples.

* * * * *